United States Patent [19]

McCarthy et al.

[11] Patent Number: 5,125,035
[45] Date of Patent: Jun. 23, 1992

[54] FIVE AXIS GENERATED HOLE INSPECTION SYSTEM

[75] Inventors: Terrence McCarthy, Bergenfield; Gerard Haring, Old Tappan, both of N.J.

[73] Assignee: Chromalloy Gas Turbine Corporation, Orangeburg, N.Y.

[21] Appl. No.: 671,168

[22] Filed: Mar. 15, 1991

Related U.S. Application Data

[63] Continuation of Ser. No. 452,682, Dec. 18, 1989, abandoned.

[51] Int. Cl.⁵ .............................................. G06K 9/00
[52] U.S. Cl. ....................................... 382/8; 358/101; 358/106; 361/474.34
[58] Field of Search ............... 382/1, 8; 358/101, 106, 358/107; 364/474.34

[56] References Cited

U.S. PATENT DOCUMENTS

| | | | |
|---|---|---|---|
| 2,684,009 | 7/1954 | Malsbary | 356/400 |
| 4,184,175 | 1/1980 | Mullane, Jr. | 358/106 |
| 4,185,298 | 1/1980 | Billet et al. | 358/106 |
| 4,379,308 | 4/1983 | Kosmowski | 358/7 |
| 4,555,798 | 11/1985 | Broadbent Jr. et al. | 382/8 |
| 4,596,037 | 6/1986 | Bouchard et al. | 382/8 |
| 4,672,676 | 6/1987 | Linger | 382/8 |
| 4,776,022 | 10/1988 | Fox et al. | 382/8 |
| 4,803,639 | 2/1989 | Steele et al. | 378/58 |
| 4,807,296 | 2/1989 | Ando et al. | 382/8 |

Primary Examiner—Michael Razavi
Attorney, Agent, or Firm—Mitchell D. Bittman

[57] ABSTRACT

A system for automatically inspecting the true position of cooling holes manufactured in hot section turbine blades and vanes. The system includes a computer controlled rotary tilt table for correctly positioning the blade or vane having the cooling holes, and computer controlled, a coordinate measuring machine for positioning a video camera in the X, Y, Z directions so that it can look straight into the selected cooling hole of the blade or vane. An image analyzer receives the image from the video camera, calculates the centroid of the image, and the host computer calculates and reports deviation between the actual or true position of the cooling hole and data relating to the correct position of the same. A touch probe is also provided with the coordinate measuring machine to verify the correct position of the blade or vane prior to imaging.

10 Claims, 4 Drawing Sheets

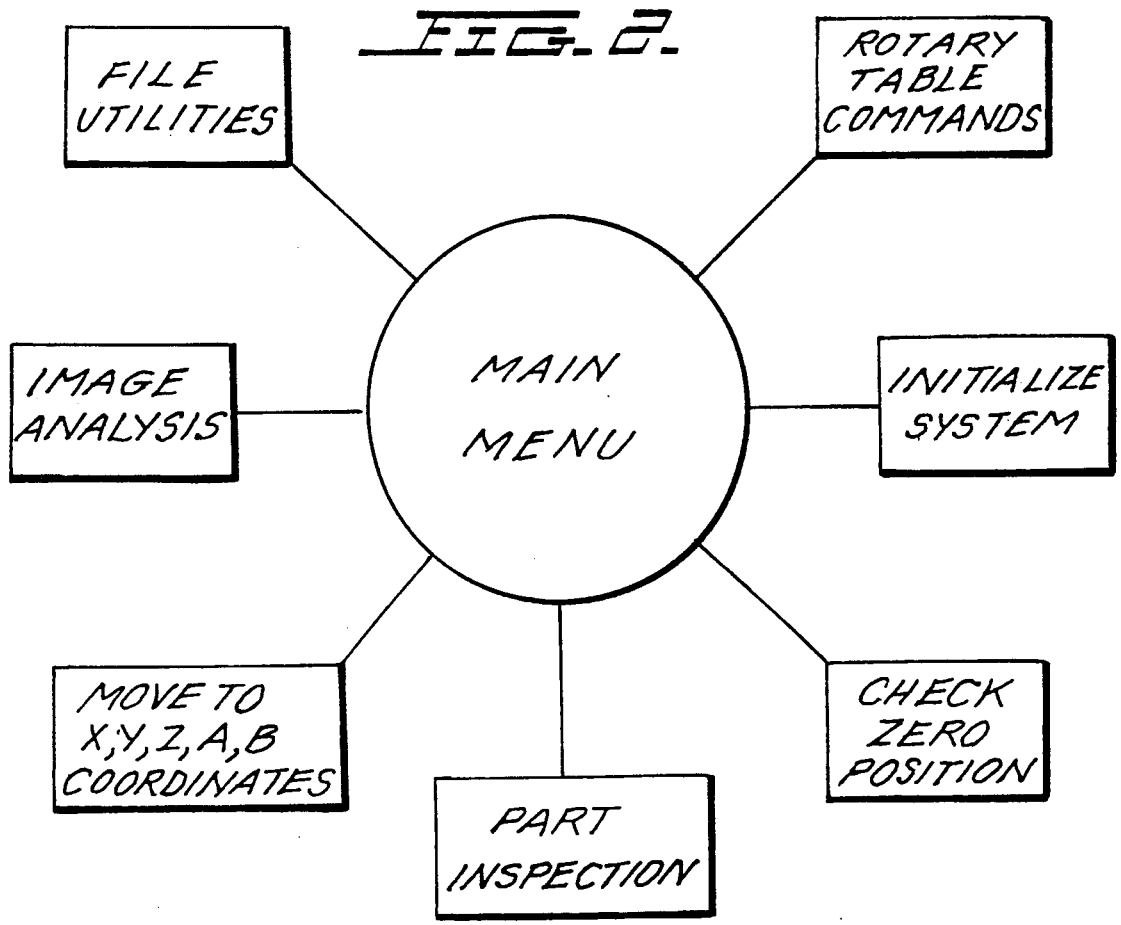
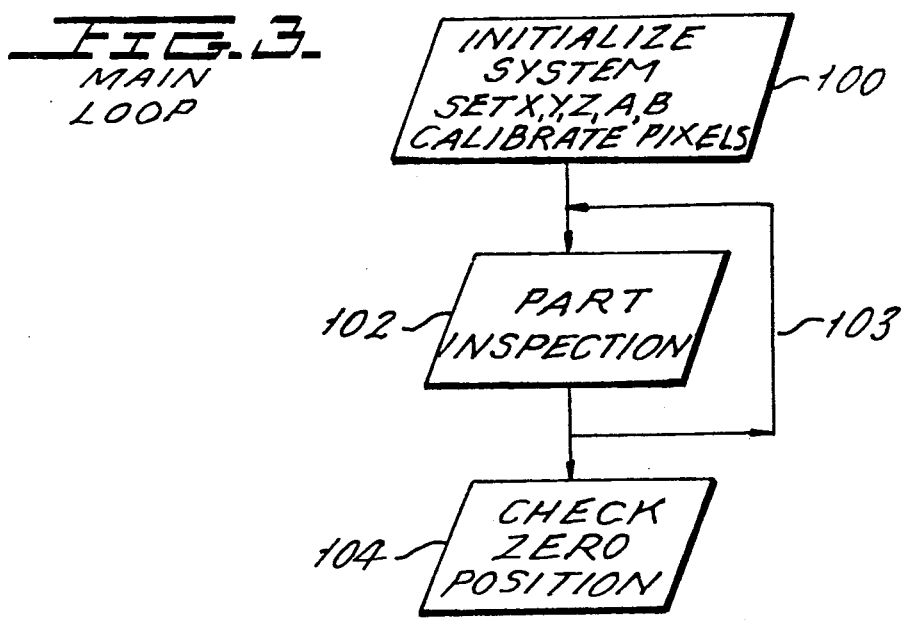

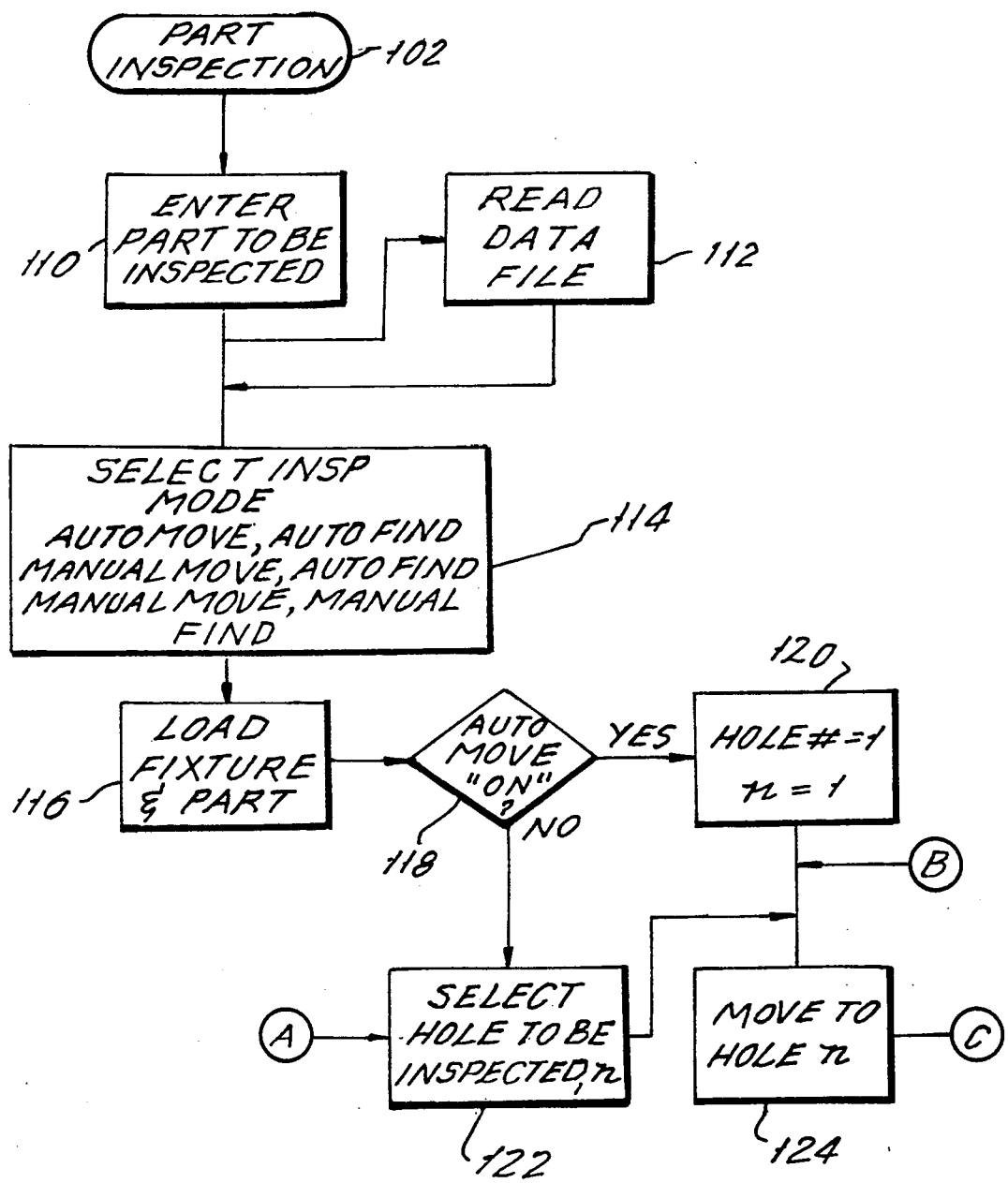

FIVE AXIS GENERATED HOLE INSPECTION SYSTEM

This is a continuation of application Ser. No. 071452,682, filed Dec. 18, 1989 and now abandoned.

BACKGROUND OF THE INVENTION

1. Field of the Invention

The present invention relates to a system which automatically inspects the true position and size at point of entry of holes, more specifically, the position and size of cooling holes manufactured in "hot section" turbine blades and vanes of jet engines.

2. Description of the Related Prior Art

Cooling holes are manufactured in airfoils of jet engines to distribute cooling air over the active surface of the airfoil, via a diffuser formation extending laterally and downstream from the discharge end of each of a plurality of the cooling holes.

For a detailed discussion of such holes and methods by which they are manufactured, reference may be had to U.S. Pat. No. 4,197,443. The particular technique of that patent involves electric-discharge machining (EDM) of cooling holes wherein a single electrode is so configured as to form both the cooling hole and its diffusion area. This patent also teaches that a single such electrode may comprise comb-like formations whereby a single EDM stroke may develop and form both the hole and the diffuser for each of an arrayed plurality of holes and associated diffusers in a single blade.

Another process for forming cooling holes in airfoils is laser drilling as taught in U.S. Pat. No. 4,808,785, which discloses a two-step process including laser drilling a hole in an airfoil and subsequently performing an EMD step to form the diffuser shaped part of the hole.

Regardless of how the cooling holes are manufactured in the airfoil, they must be inspected to check their true position as compared to their correct position. The present industry methods for measuring the true position and size at point of entry of cooling holes involves either a surface plate layout method or a comparator method.

In the surface plate layout method, the blade or vane having the cooling holes manufactured therein is mounted in a stage. A scratch line is made on the blade or vane where the correct X coordinate of the hole should be located, and a scratch line is also made on the blade or vane where the correct Y coordinate of the hole should be located. The blade or vane is then inspected to see if the intersection of the scratch lines corresponds to the actual position of the hole. Alternatively, a pin is placed in the cooling hole and the blade or vane is rotated and tilted to an angle so that the pin is parallel to a table upon which the stage holding the blade or vane is seated. The X Y distance of the pin from a specified point on the blade or vane is then measured, and the deviation of the position of the true hole from its correct position can be determined. These types of surface plate layout methods, however, are generally unsatisfactory since they are based upon manual operation of the various elements and, as such, precise inspection cannot be achieved.

In the comparator method, light is reflected off the blade or vane and is projected onto a screen having an overlay showing the correct position of the cooling holes for that blade or vane. Deviation of the true position of the cooling holes from their correct position shows on the overlay. This method, however, is not precise due to the compound reflection angles involved. Furthermore, this method requires precise charts and dedicated tooling.

SUMMARY OF THE INVENTION

The present invention overcomes the deficiencies of the above-noted prior art by providing a system which accurately and automatically inspects the true position of cooling holes in hot section turbine blades and vanes of jet engines.

The system of the present invention includes a rotary tilt table for mounting the part and positioning the part at a predetermined, rotational and tilted position for inspection of a selected hole in the part. A video camera, movable by a coordinate measuring machine in the X, Y, and Z directions, images a selected hole. An image analyzer enchances the image and calculates the position of a centroid of the image. A host computer is used to automatically rotate and tilt the rotary tilt table and to control movement of the video camera to the appropriate position over each hole in accordance with reference data supplied by the aircraft engine manufacturer. The host computer is also used to compare the position of the centroid of the image with data relating to the correct position of the centroid, and report deviation between the same.

A method for automatically inspecting the true position and size of holes is also provided. The method includes driving a rotary tilt table to a predetermined rotational and tilted position under computer control in accordance with predetermined coordinates. A video camera is then moved over the particular hole to be inspected by a computer controlled coordinate measuring machine in accordance with the predetermined coordinates from the computer. The image of the selected hole is then enhanced and the position of a centroid of that image is calculated by an image processor. The centroid position of the selected hole is compared by the computer with data relating to the correct centroid position for that hole, and deviations between the same are calculated and reported by the computer. The position of the part may be verified by touch probe sensing prior to imaging.

BRIEF DESCRIPTION OF THE DRAWINGS

Other features and advantages of the present invention will become apparent when the following description is read in conjunction with the accompanying drawings in which:

FIG. 2 is a flow chart of the "MAIN MENU" of the system showing various functions of the system available to an operator.

FIG. 3 is a flow chart of the "MAIN LOOP" of the system.

FIG. 4 is a flow chart showing the first part of the inspection subroutine of the "MAIN LOOP" shown in FIG. 3.

DETAILED DESCRIPTION OF THE PREFERRED EMBODIMENTS

Figure 1:
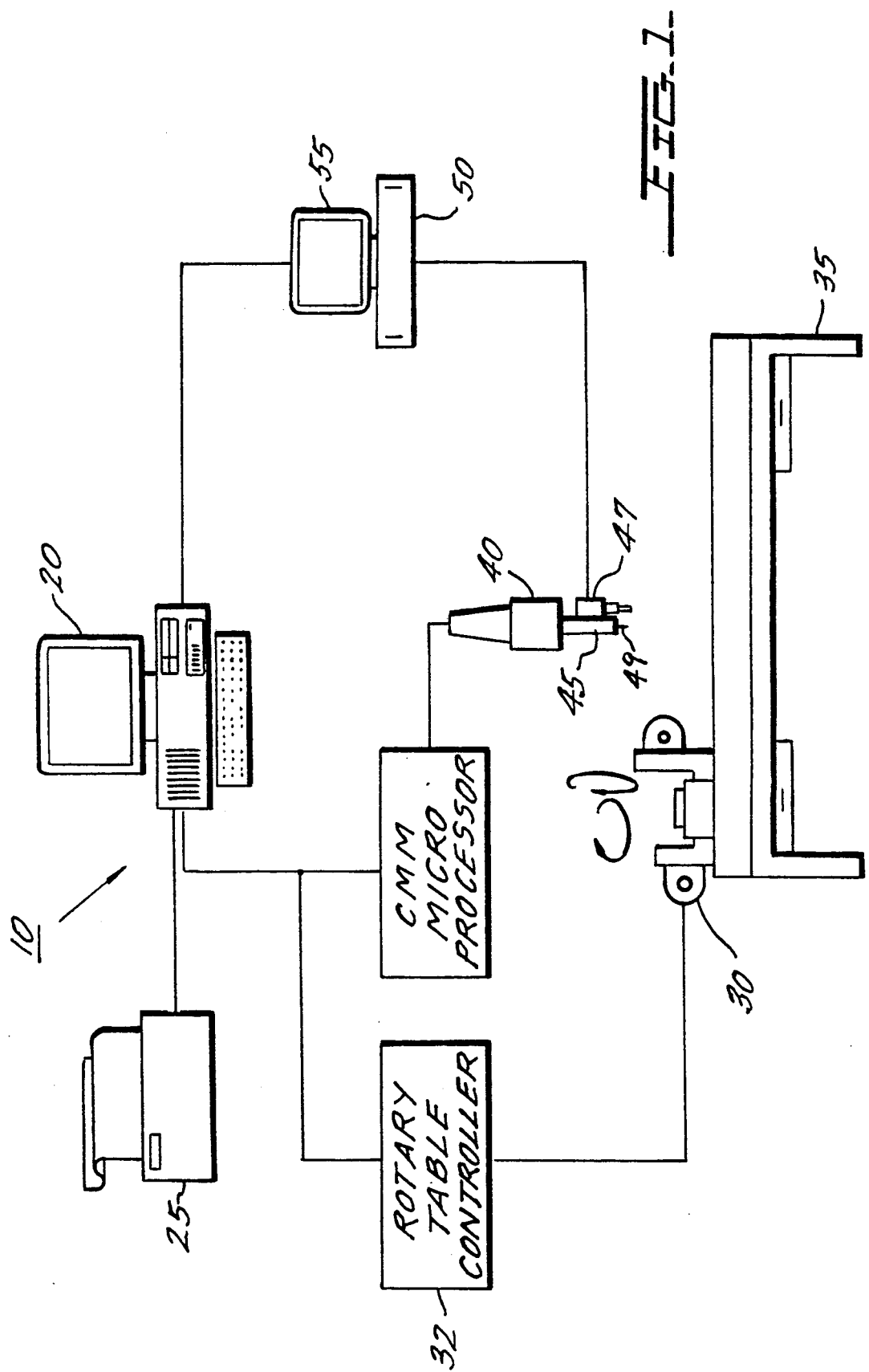
FIG. 1 shows the inconnection of the components in the system of the invention.

Referring first to FIG. 1, the system of the invention, identified generally by reference numeral 10, has four primary components: a computer 20; a two-axes rotary tilt table 30; a video camera mounted on a coordinate measuring machine 40; and an image processor 50.

The inspection of the cooling holes by system 10 can be done automatically under control of computer 20, semiautomatically with operator assistance, or manually by an operator as described in further detail below.

Computer 20 is coupled for communication with the rotary tilt table 30, coordinate measuring machine (CMM) 40, and an image processor 50. Rotary tilt table 30 is used to precisely mount and position a blade or vane, and is suitably positioned on a table 35, as shown in FIG. 1. A rotary table controller 32 (shown in block diagram form) provides a digital interface between computer 20 and rotary tilt table 30. Similarly, microprocessor 42 of CMM 40 provides an interface between this unit and computer 10. Mounted to a Z-arm portion 45 of the CMM 40 is a video camera 47, preferably a CCD square pixel camera, for recording an image of a selected cooling hole. Camera 47 sends video signals to image processor 50 over suitable electrical cables. Image processor 50 enhances the image on a video monitor 55. The centroid of the enhanced image is calculated by image processor 50 and sent to computer 20 for comparison with the correct centroid position for that cooling hole.

The individual components of the invention will now be described in greater detail.

Computer 20 acts as a host computer for system 10. As will be described below, it controls the movement of rotary tilt table 30 and CMM 40 to properly position and image a selected hole. It also stores predetermined coordinates for the holes in a data file, calculates deviations between the expected and the actual location of the holes, and archives inspection data in a disk file for statistical purposes. Any suitable personal computer such as an IBM PC, XT or AT, which is compatible with the other devices of the system, may be utilized. A line printer 25 is coupled to personal computer 20 for making hard copies of inspection results and other data when desired.

Rotary tilt table 30 is a computer numeric control (CNC), two-axes table. As shown by the arrows in FIG. 1, the table can rotate and tilt. A turbine blade or vane is mounted in a stage in a very precise manner utilizing a clamp, as is conventional. The stage and blade or vane mounting is then secured on the rotary table 30 and the rotary and tilt positions of table 30 are adjusted automatically by personal computer 20 (or manually by the operator) in accordance with the predetermined rotary and tilt coordinates for that particular part. A perferred rotary tilt table for use in the invention is one from the RS-8 series of Roto-Technology, Inc., 351 Fame Rd., Dayton, Ohio 45449. These tables have an accuracy of 3 arc-seconds, and are especially suitable for use in the invention.

Once the part to be inspected is rotated and titled to the correct position, CMM 40 must correctly position video camera 47 so that the particular hole to be inspected can be viewed in a "straight-in" manner. CMM 40 is a direct computer controlled, coordinate measuring machine which operates under control of computer 20. The CMM is positionable in the three directions, X, Y and Z, and, in combination with the two directions of movement A, B from rotary tilt table 30, achieves the five axes positioning of the system 10. The preferred CMM for use in the present invention is one of the "Cordax ® 1800 Series" available from Sheffield Measurement, P.O. Box 1127, Dayton, Ohio, 45401-1127. The preferred CMM has an accuracy of 0.0005 inches and a repeatability of 0.0001 inches.

Mounted to a Z-arm portion 45 of CMM 40 is video camera 47, which, as stated previously, preferably uses a charge coupled device (CCD) to image the hole to be inspected. Movement of video camera 47 by CMM 40 in the Z axis toward and away from the blade or vane allows for focusing of video camera 47 upon the cooling hole to be inspected. Video camera 47 relays the focused image of the hole to image processor 50. The Z-arm portion 45 of CCM 40 is also provided by the manufacturer with a touch probe 49, which may advantageously be used (under control of host computer 20 in accordance with stored data) to verify that the part is properly positioned.

Image processor 50 is used to enhance the contrast of the cooling hole from the surrounding surface, producing a binary image. Image processor 50 also automatically calculates the centroid position of the image, thus closely approximating the actual center of the hole. A video monitor 55 and a "mouse" are provided so that an operator may alternatively create a crosshatch screen superposed on the binary image and move a cursor on the screen to the centroid position of the binary image displayed on monitor 55 to manually locate the centroid position. Appropriate software (available from the supplier of the image processor) is utilized to create the grid on the screen. In any event, the centroid position is reported by the image processor 50 to personal computer 20.

The preferred image processor for use in the invention is the "Model 3000 Image Analysis System", available from Image Technology Corp., 992 Grand Blvd., Deer Park, N.Y., 11729. This particular image processor can be used with an IBM PC, XT or AT or compatible personal computer. Since this processor digitizes the image, the present invention may be interfaced with CAD and CNC systems.

The automatic operation of system 10 will now be described.

In general, when a cooling hole is selected for inspection, host computer 20 drives the rotary tilt table 30 to its appropriate A, B angles. Host computer 20 also sends commands to CMM 40 to position the video camera to a particular set of X, Y and Z coordinates. At this time, the cooling hole image is imaged by CCD camera 47 and this image is sent to image processor 50. Image processor 50 enhances the contrast between the hole and the surrounding surface, producing a binary image of the same. The centroid of this binary image is calculated by image processor 50 and relayed to host personal computer 20, which compares the calculated centroid coordinates with customer supplied data and reports deviations.

The operation of system 10 will now be described in flow chart form.

Initially, an operator views a "MAIN MENU" screen on a monitor associated with personal computer 20, as shown in block diagram in FIG. 2. The operator may: initialize the system; check the zero position of the system; inspect a part; move CMM 40 to X, Y, and Z coordinates and table 30 to A (rotary) and B (tilt) coordinates; control image analysis; access certain file utilities; and control the rotary table.

The system operates in a "MAIN LOOP" as shown in FIG. 3, whereby in step 100, the operator first initializes the five axes of the system, i.e., sets the X, Y, Z, A, and B coordinates, and calibrates pixels of the image processor 50. Part inspection then commences in step 102 in one of several modes and each cooling hole is inspected as shown by the loop 103 of FIG. 3. After part inspection is completed, system 10 returns to a "check zero position" in step 104. The system checks zero and recalibrates on a pre-programmed time interval or upon command at operator discretion.

The part inspection subroutine 102 is shown in FIG. 4. Previously, customer supplied hole data is inputted into computer 20 via a keyboard or a data disk. In step 110, the operator keys the part to be inspected into computer 10. In step 112, system 10 reads a data file of the previously entered customer supplied information corresponding to the correct position of cooling holes for that part. The operator then (in step 114) selects a particular inspection mode from the following: a) fully automated inspection or "AUTO MOVE, AUTO FIND", where system 10 locates all holes and reports data; b) individual hole inspection or "MANUAL MOVE, AUTO FIND", where the operator selects a hole, and system 10 locates and reports data; c) semiautomatic inspection or "AUTO MOVE, MANUAL FIND", where system 10 automatically moves to a particular set of coordinates, the operator locates the hole, and system 10 reports data; or d) manual inspection or "MANUAL MOVE, MANUAL FIND", where the operator selects and locates a hole, and system 10 reports data. At this time (step 116), the stage holding the part to be inspected is mounted onto rotary tilt table 30 and the actual part inspection commences.

Figure 5:
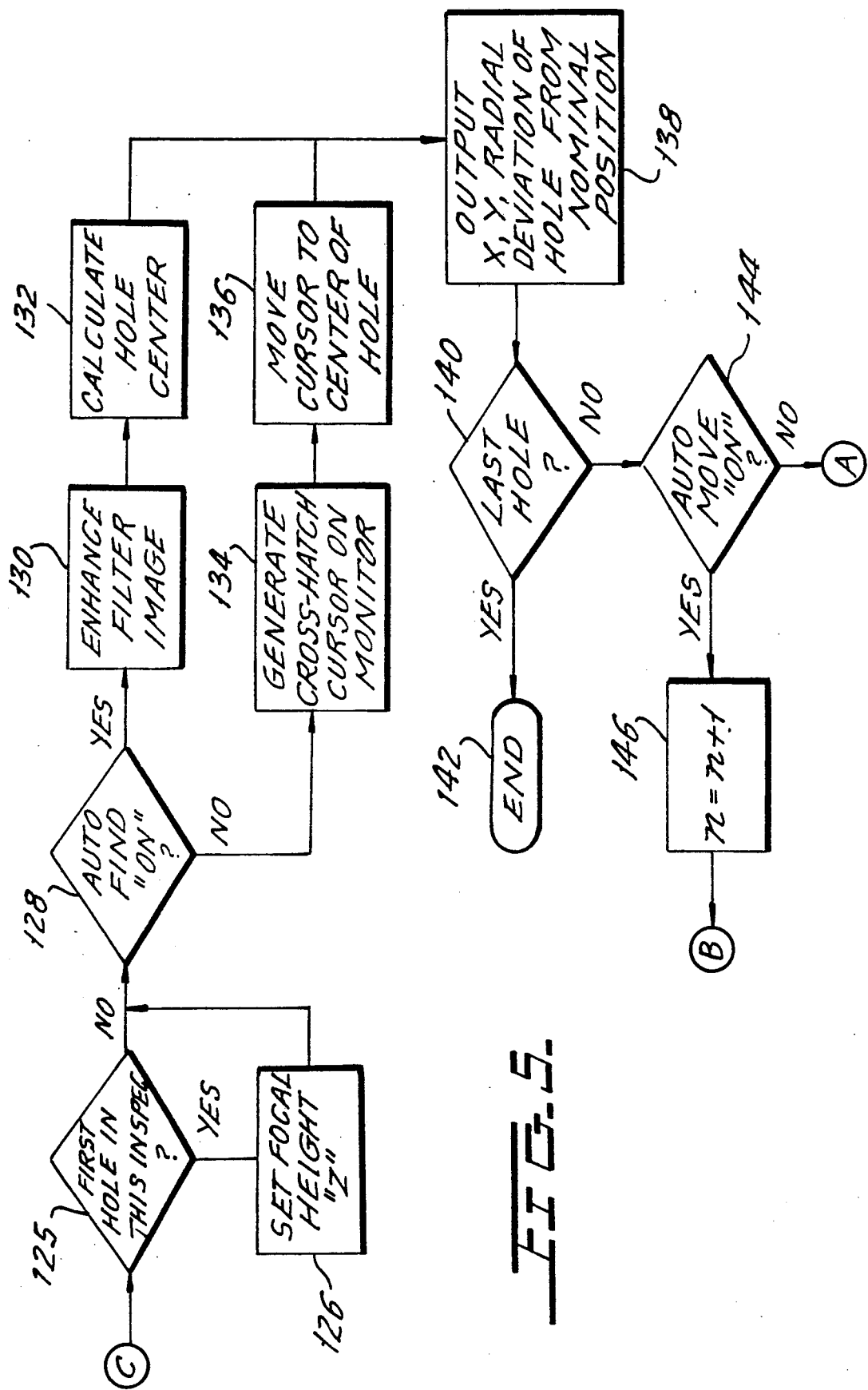
FIG. 5 is a flow chart shown the second part of the inspection subroutine shown in FIG. 3.

The software in computer 20 first checks to see if the "AUTO MOVE" has been selected (step 118). If the "AUTO MOVE" function is selected or "on", system 10 will proceed with inspection of hole "n" (step 120). If not, the operator is queried to select the hole to be inspected (step 122). Once a hole has been selected (whether automatically or manually), computer 20 then sends out appropriate commands to rotary tilt controller 32 and CMM 40 to position the part at the correct rotational and tilt angles and the video camera at the correct X-Y coordinates, for inspection of hole n (step 124). If this is the first hole in the inspection (step 125), the focal height Z of the CMM 40 carrying the CCD camera 47 is adjusted accordingly (step 126, FIG. 5). In step 128, the computer 10 checks if "AUTO FIND" has been selected by the operator. If so, an enhanced filter image is produced (step 130) and the image processor 50 calculates the hole center or centroid (step 132). If the "AUTO FIND" mode is not on, image processor 50 generates, on monitor 55, a crosshatch screen superimposed on the displayed image and a cursor (step 134), and the operator moves the cursor to the center of the hole imaged on monitor 55 (step 136). Coordinates of the centroid position, whether calculated by image processor 50 or manually by the operator moving the cursor are relayed to personal computer 20.

In step 138, computer 20 computes the X Y radial deviation of the actual hole from its nominal position, and stores this information. Computer 20 then checks to see if the hole just inspected is the last hole (step 140). If so, the inspection stops (step 142). If additional holes are to be inspected, the software directs computer 20 to check again as to whether "AUTO MOVE" has been selected (step 144). If so, computer 20 increments to the next hole i.e., the "n+1" hole (step 146), and inspection of that hole commences with step 124 in the manner described above. If "AUTO MOVE" is not selected, the operator is queried to select the hole to be inspected (step 122), and inspection of that hole commences. The above-described loop is repeated until all cooling holes have been inspected.

The table below shows, by way of example, the information that would be reported by computer 20 in accordance with the above-described operation. As shown in this example, holes 1 thru 6 were inspected and their respective deviations from the X and Y coordinates of the correct cooling hole position were measured. The radial deviation calculated by personal computer 20 is shown as "RADIAL DEV". As can be seen, all but one of the values of radial deviation were acceptable:

TABLE

| HOLE | X DEV  | Y DEV  | RADIAL DEV |
|------|--------|--------|------------|
| 1    | +0.003 | −0.003 | +0.004 Ok  |
| 2    | −0.004 | +0.002 | +0.004 Ok  |
| 3    | +0.005 | −0.003 | +0.006 Ok  |
| 4    | +0.001 | −0.005 | +0.005 Ok  |
| 5    | +0.009 | −0.005 | +0.011 **  |
| 6    | +0.007 | −0.007 | +0.010 Ok  |

Although the present invention has been described in connection with a preferred embodiment thereof, many other variations and modifications will now become apparent to those skilled in the art without departing from the scope of the invention. It is preferred, therefore, that the present invention not be limited by the specific disclosure herein, but only by the appended claims.

What is claimed is:

1. A system for automatically inspecting the position of at least one selected hole of a plurality of holes manufactured in a curved surface of a turbine blade or vane, comprising;
   means for rotating the turbine blade or vane in a first axis and tilting the turbine blade or vane in a second axis different from said first axis to a predetermined rotated and tilted position for inspection of the selected hole;
   means for imaging the selected hole, and means for moving the means for imaging in X, Y and Z directions, so that the means for imaging is positioned over and focussed on the selected hole;
   means for processing the image from said means for imaging, including calculating the position of the centroid of the selected hole from said image; and
   a host computer controlling the positioning means, the means for moving the imaging means, and the processing means in accordance with predetermined data stored in said host computer relating to the correct position of the selected hole, the host computer being programmed to receive the position of the centroid of a selected hole calculated by said processing means and to compare the position of the centroid of the selected hole with the data stored in the host computer relating to the correct position of the selected hole and to report deviations between the calculated centroid and the data.

2. The system of claim 1, wherein the means for rotating and tilting comprises a rotary tilt table adapted to be controlled by the host computer and to automatically rotate and tilt in response to commands from the host computer.

3. The system of claim 1, wherein the means for moving the means for imaging comprises a coordinate measuring machine adapted to be controlled by the host computer and to be automatically driven to the X, Y and Z coordinates by the host computer, and wherein the means for imaging comprises a video camera for producing an image of the selected hole.

4. The system of claim 3, wherein the coordinate measuring machine includes a Z-arm portion and the video camera is mounted on the Z-arm portion, the Z-arm portion being moved by said coordinate measuring machine such that the distance between the video camera and the selected hole corresponds to the focal length of the video camera.

5. The system of claim 1, wherein the processing means comprises an image processor, the image processor being adapted to send to the host computer the centroid of the selected hole for the comparison with the predetermined data.

6. The system of claim 5, wherein the image processor is coupled to a video monitor for displaying the image of the selected hole, the image processor being adapted to form a grid on the image displayed on the video monitor and a cursor which is movable onto the image for an operator to manually locate the centroid of the image.

7. The system of claim 1, wherein the host computer is a personal computer adapted for controlling the positioning means, the means for moving the imaging means and the image analyzing means according to the predetermined rotary, tilt, X, Y and Z coordinates.

8. The system of claim 7, further comprising a printer coupled with the personal computer for outputting information calculated by the system.

9. A method for automatically inspecting the position of at least one selected hole of a plurality of holes manufactured in a curved surface of a turbine blade or vane, comprising the steps of:

mounting said turbine blade or vane on a rotary tilt table and rotating the rotary tilt table to a predetermined rotated position in a first axis and tilting the rotary tilt table to a predetermined tilted position in a second axis, the first axis being different from the second axis, under control of a host computer in accordance with predetermined rotary and tilt coordinates entered into the host computer to position a selected hole for inspection;

moving a video camera to a predetermined X, Y, and Z position with respect to the selected hole under control of the host computer in response to predetermined X, Y and Z coordinates stored in the host computer;

imaging the selected hole using the video camera and relaying the image of the selected cooling hole to an image processor;

calculating the centroid position of the selected hole from the image in the image processor and relaying the calculated centroid position of the selected hole to the host computer;

comparing the position of the centroid calculated by the image processor with data relating to the correct position of the selected hole using the host computer; and reporting deviations between the position of the selected hole and the data relating to the correct position of the selected hole using the host computer.

10. A method as recited in claim 9, further comprising the step of verifying the position of said turbine blade or vane mounted on said rotary tilt table with a touch probe after said part is mounted and prior to said step of imaging.

* * * * *